United States Patent [19]

Biftu et al.

[11] Patent Number: 4,595,693
[45] Date of Patent: Jun. 17, 1986

[54] METHOD OF USE OF 2,5-DIARYL TETRAHYDROFURANS AND ANALOGS THEREOF AS PAF-ANTAGONISTS

[75] Inventors: Tesfaye Biftu, Westfield; Thomas W. Doebber, Scotch Plains; San-Bao Hwang, Scotch Plains; Thomas R. Beattie, Scotch Plains; Tsung-Ying Shen, Westfield, all of N.J.; Robert Stevenson, Lexington, Mass.

[73] Assignee: Merck & Co., Inc., Rahway, N.J.

[21] Appl. No.: 617,294

[22] Filed: Jun. 4, 1984

[51] Int. Cl.$^4$ ............................................. A61K 31/34
[52] U.S. Cl. .................................... 514/461; 549/487; 549/491; 514/229; 549/492; 549/494; 514/231; 549/497; 549/498; 514/233; 549/499; 514/234; 549/500; 514/236; 549/501; 549/502; 514/237; 549/504; 514/239; 514/333; 514/336; 514/422; 514/444; 514/452; 514/464; 514/466; 514/471; 514/473; 544/105; 546/256; 546/281; 546/283; 548/517; 548/518; 549/60; 549/362; 549/429; 549/435; 549/472; 549/473; 549/475; 549/483; 549/485; 549/486

[58] Field of Search ................. 549/60, 362, 429, 435, 549/472, 473, 475, 483, 485, 486, 487, 491, 492, 494, 497, 498, 499, 500, 501, 502, 504; 548/517, 518; 546/256, 281, 283; 544/105; 514/229, 231, 233, 234, 236, 237, 239, 333, 336, 422, 444, 452, 461, 464, 466, 471, 473

[56] References Cited

PUBLICATIONS

Biftu et al., J. Chem. Soc., 1147 (1978).
Biftu et al., J. Chem. Soc., 2276 (1979).
Sarkanen et al., J. Chem. Soc. (1973) pp. 1869-1878.
Perry et al., J. Org. Chem., vol. 37 (1972) pp. 4371-4376.
Ahmed et al., Tetrahedron, vol. 32 (1976) pp. 1339-1344.

*Primary Examiner*—Richard L. Raymond
*Attorney, Agent, or Firm*—Theresa Y. Cheng; Michael C. Sudol

[57] ABSTRACT

Analogs of 2,5-Diaryl tetrahydrofurans which were substituted or unsubstituted at 3,4-positions were prepared.

These compounds are found to have potent and specific PAF (Platelet Activating Factor) antagonistic activities and thereby useful in the treatment of various diseases or disorders mediated by the PAF, for example, inflammation, cardiovascular disorder, asthma, lung edema, adult respiratory distress syndrome, pain, and aggregation of platelets.

3 Claims, No Drawings

METHOD OF USE OF 2,5-DIARYL TETRAHYDROFURANS AND ANALOGS THEREOF AS PAF-ANTAGONISTS

BACKGROUND OF THE INVENTION

Platelet-activating factor (PAF) has recently been identified as an acetyl glyceryl ether phosphorylcholine (AGEPC), i.e., 1-O-hexadecyl/octadecyl-2-acetyl-sn-glyceryl-3-phosphorylcholine (Hanahan D. J., et al., *J. Biol. Chem.* 255: 5514, 1980). Even before its chemical identification, PAF had been linked to various biological activities and pathways making it one of the important mediators responsible for a variety of physiological processes including activation of coagulation of platelets, pathogenesis of immune complex deposition, smooth muscle contraction, inflammation, pain, edema as well as respiratory, cardiovascular and intravascular alterations. Since these physiological processes are in turn associated with a large group of diseases, for example, inflammatory disease, cardiovascular disorder, asthma, lung edema, and adult respiratory distress syndrome, more and more scientific investigation has been focused on the search of a PAF-antagonist or inhibitor for treating or preventing these common diseases.

The compounds of the present invention are specific PAF-antagonists. They are similar to a subclass of compounds called lignans which characteristically contain two phenylpropyl groups bonded at the β-carbon. Tetrahydrofuran (THF) lignans can exist in six different stereoisomers as shown in Scheme I.

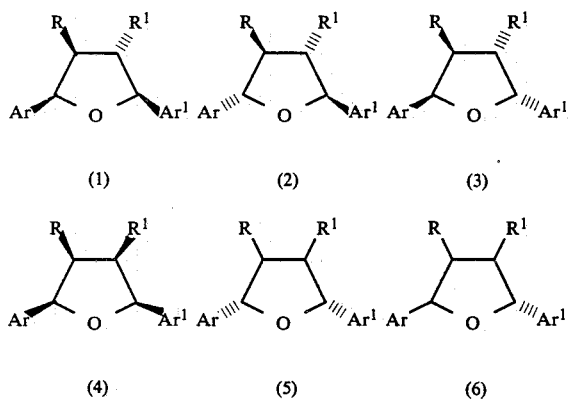

(1)      (2)      (3)

(4)      (5)      (6)

One of these THF lignans (+) r-2,5c-bis(3,4-dimethoxyphenyl)-3c,4t-dimethyl tetrahydrofuran, known as veraguensin, was first isolated in 1962 from the plant *Octoea veraguensis*. (N. S. Crosley and C. Djerassi, *J. Chem. Soc.*, 1962, 1459).

We have prepared all the possible isomers of the tetrahydrofuran lignan analogs [T. Biftu, B. G. Hazra and R. Stevenson, *J. Chem. Soc.*, 1978 (1147), T. Biftu, B. G. Hazra and R. Stevenson, *J. Chem. Soc.*, 1979 (2276), C. W. Perry et al, *J. Org. Chem.*, 1972 (4371), R. Stevenson et al, *Tetrahedron*, 1976 (1339), 1977 (285), F. A. Wallis et al, *J. Chem. Soc.*, 1973 (1869) and references cited in there] with different substituents and found that the meso-cis isomer (4) is the most potent and specific PAF-antagonist.

Accordingly, it is the object of the present invention to prepare the most potent isomers of known or novel tetrahydrofuran derivatives as PAF-antagonists and use them for the treatment of various diseases including prevention of platelet aggregation, hypertension, inflammation, asthma, lung edema, adult respiratory distress syndrome, cardiovascular disorder and other related skeletal-muscular disorders.

Another object of the present invention is to develop processes for the preparation of each and every stereoisomer of the 2,5-diaryltetrahydrofuran analogs.

A further object of the present invention is to provide acceptable pharmaceutical compositions containing one or more of the tetrahydrofuran derivatives and/or analogs as the active ingredient. As PAF-antagonists, these novel compositions should be effective in the treatment of various skeletal-muscular related diseases.

Finally, it is the ultimate object of this invention to provide a method of treatment comprising the administration of a therapeutically sufficient amount of these PAF antagonists to a patient suffering from various skeletal-muscular disorders including inflammation, e.g., osteoarthritis, rheumatoid arthritis and gout, hypertension, asthma, pain, lung edema, or adult respiratory distress syndrome or cardiovascular disorder.

DETAILED DESCRIPTION OF THE INVENTION

A. Scope of the Invention

This invention relates to PAF-antagonists of the structural formula

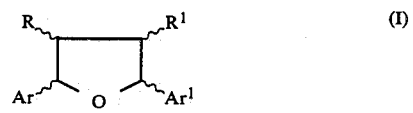

wherein R is:
(a) hydrogen;
(b) lower alkyl of 1–6 carbon atoms, e.g. methyl, ethyl, isopropyl, butyl, pentyl or hexyl;
(c) haloloweralkyl especially $C_{1-6}$ haloalkyl, for example, trifluoromethyl;
(d) halo especially fluoro;
(e) COOH;
(f) $CONR^2R^3$ wherein $R^2$ and $R^3$ independently represent $C_{1-6}$ alkyl and hydrogen;
(g) —$COR^2$;
(h) loweralkenyl especially $C_{1-6}$ alkenyl e.g., vinyl, allyl, $CH_3CH=CH-CH_2-CH_2$, or $CH_3(CH_2)_3CH=CH-$;
(i) COOR° wherein R° is $C_{1-6}$ alkyl;
(j) —$CH_2OR^2$;
(k) loweralkynyl especially $C_{1-6}$ alkynyl e.g., —C≡CH;
(l) —$CH_2NR^2R^3$;
(m) —$CH_2SR^2$;
(n) =O; or
(o) —$OR^2$;
$R^1$ is loweralkyl; —COOH; or —COOR°; Ar and $Ar^1$ are the same or different from each other and are
(a) phenyl or substituted phenyl of formula

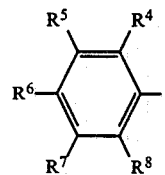

where $R^4$-$R^8$ independently represent H, $R^2O-$, $R^2S-$, $R^2SO$, $R^2SO_2-$, $CF_3O-$, $CF_3S-$, $R^2R^3N-$, $-OCH_2CO_2R^2$, $-SO_2NR^2R^3$, $-CO_2R^2$, $NR^2SO_2R^2$, $COR^2$, $NO_2$, or CN. For example, 3-methoxy-4-methylthiophenyl, 4-trifluoromethoxyphenyl, 3-methoxy-4-trifluoromethoxyphenyl, 3,4-dimethoxyphenyl, 3-methoxy-4-dimethylaminophenyl, 3,4,5-trimethoxyphenyl or $R^4-R^5$, $R^5-R^6$, $R^6-R^7$ and $R^7-R^8$ are joined together and form a bridge, for example, $-OCH_2O-$, $-OCH_2CH_2-O-$ or $-OCH_2CH_2N-$;

(b) pyrryl or substituted pyrryl;
(c) furyl or substituted furyl;
(d) pyridyl or substituted pyridyl;
(e) thiophene or substituted thiophene; or
(f) naphthyl.

The compound of formula (I) can exist in the six isomers as described in Scheme I. These various isomers bear a close relationship to the PAF-antagonistic activity observed for the compounds within the scope of this invention.

Preferably, the PAF-antagonists of this invention are of structural formulae:

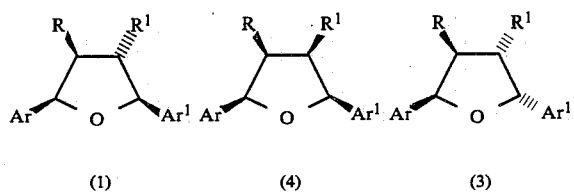

or an enantiomer thereof wherein Ar and $Ar^1$ are as previously defined.

The most active PAF-antagonist of formula (I) as defined above is cis-3,4-dimethyl-2,5-bis-(3,4-dimethoxyphenyl)tetrahydrofuran.

B. Preparation of the Compounds Within the Scope of the Invention

The PAF-antagonists of this invention have been prepared largely by stereospecific reactions from diaroylbutanes, bromo-ferulic acid derivatives or styrene derivatives as indicated in the following four schemes.

(1) Synthesis from diaroylbutanes, for example:

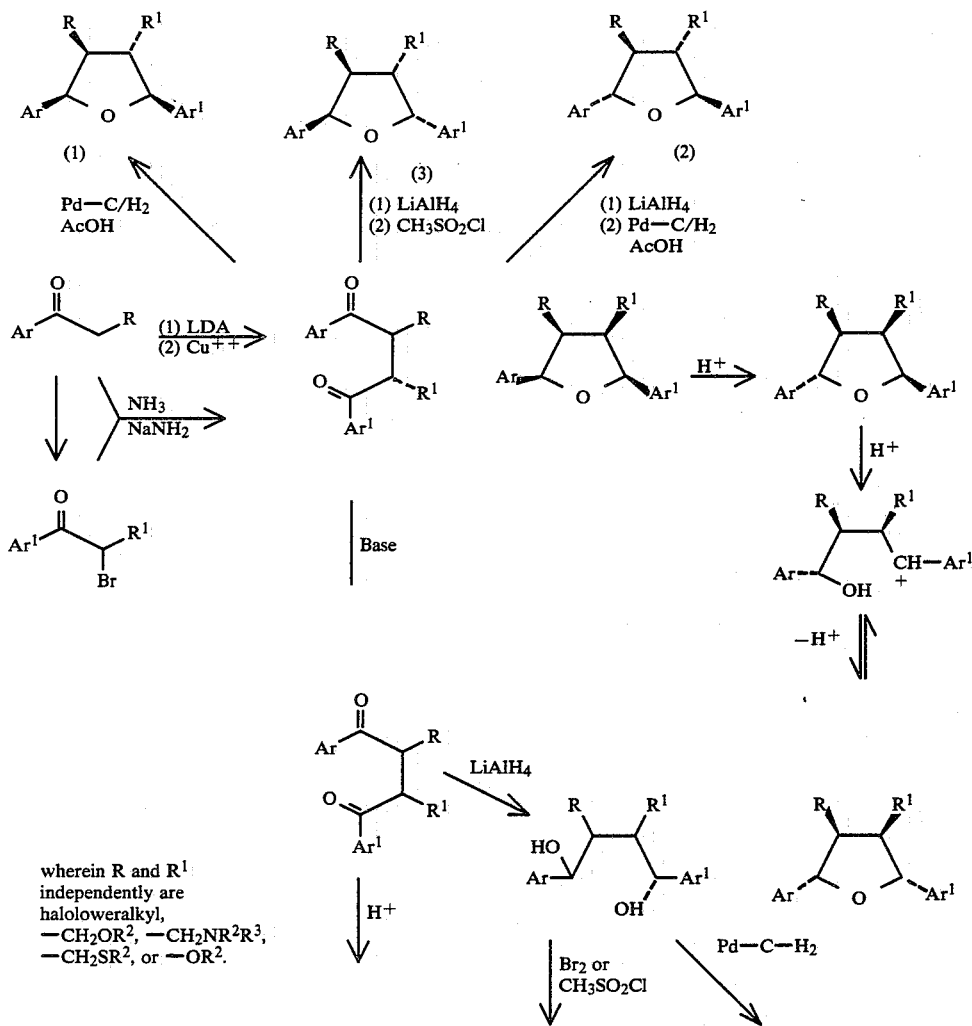

wherein R and $R^1$ independently are haloloweralkyl, $-CH_2OR^2$, $-CH_2NR^2R^3$, $-CH_2SR^2$, or $-OR^2$.

-continued
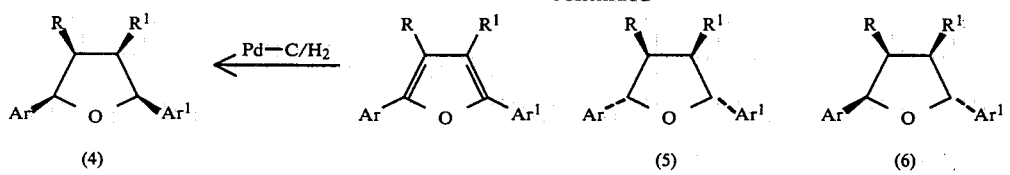
(2) Synthesis by oxidative coupling of bromo-ferulic acid derivatives, for example:
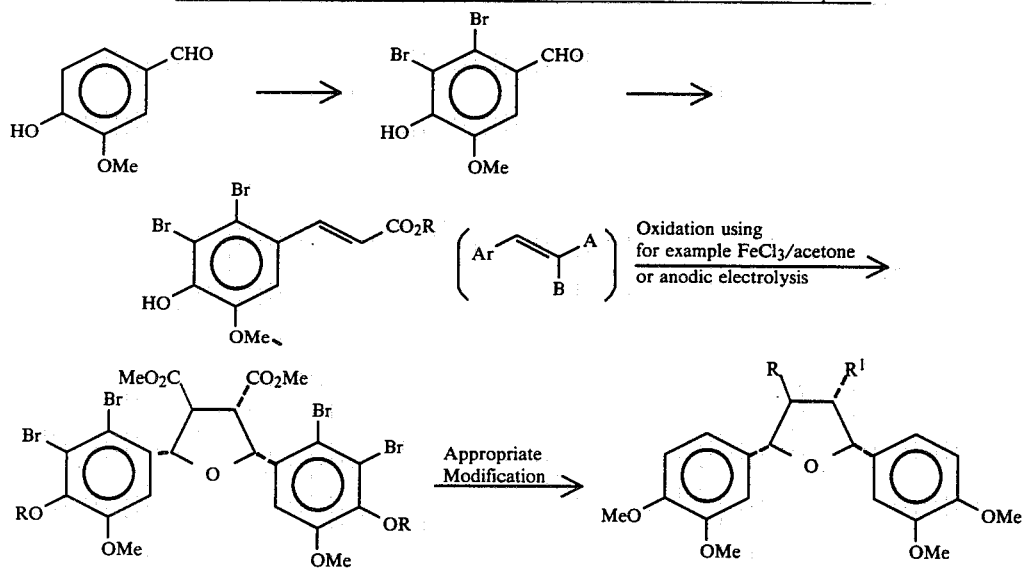
(3) Synthesis by acidic cleavage, for example:
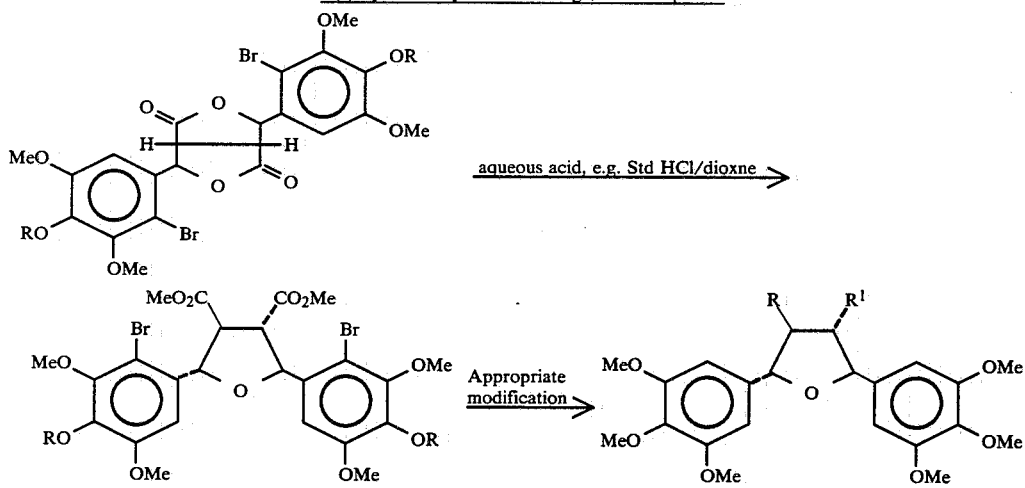
(4) Synthesis by oxidative dimerization using hydrogen peroxide catalyzed by peroxidase, for example:
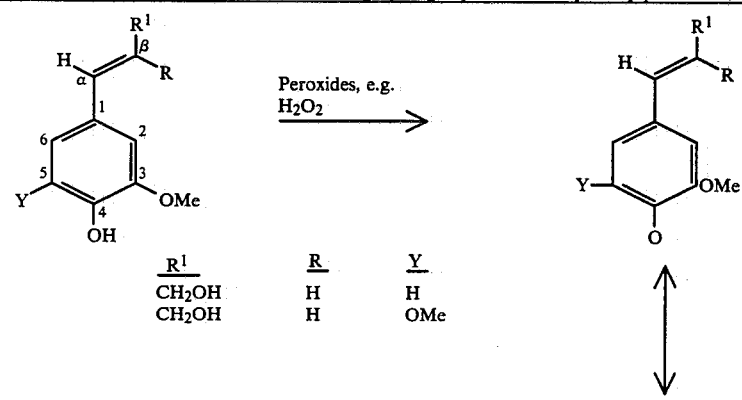
| $R^1$ | R | Y |
|---|---|---|
| $CH_2OH$ | H | H |
| $CH_2OH$ | H | OMe |

-continued

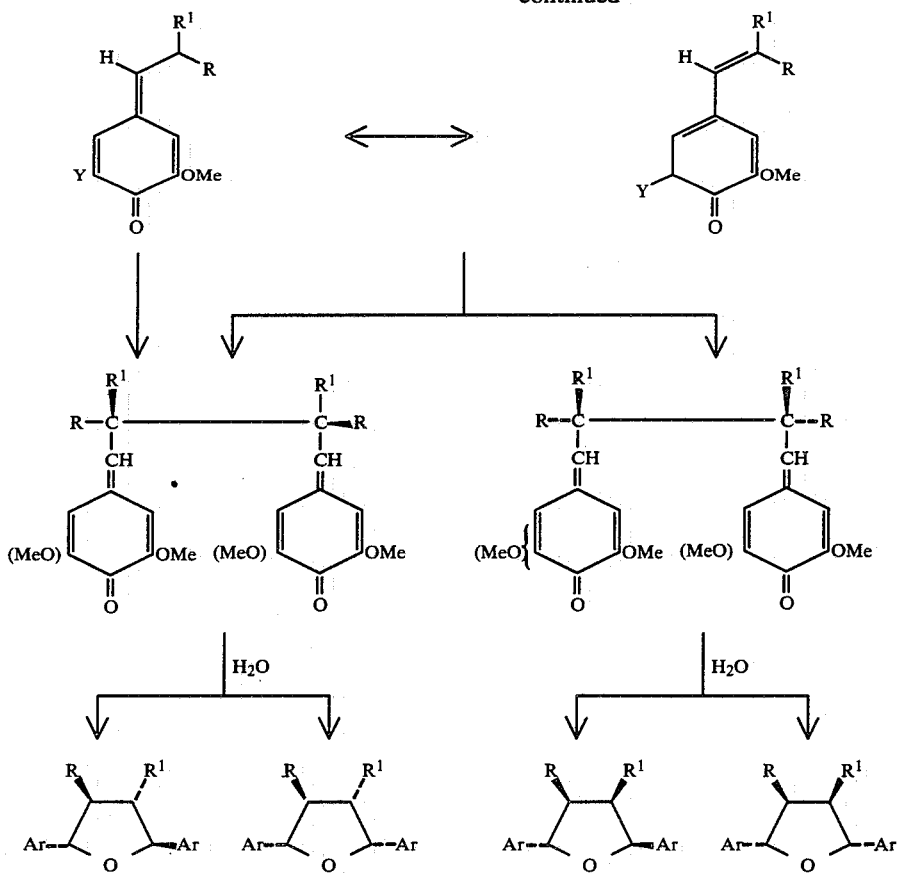

C. Utility of the Compounds Within the Scope of the Invention

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF-antagonists of formula (I) as the active constituents.

Accordingly, the compounds of Formula (I) can be used among other things to reduce pain and inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by the PAF, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspenions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.1 mg to about 140 mg per kilogram of body weight per day are useful in the treatment of the above-indicated conditions (about 5 mg to about 7 gms. per patient per day). For example, inflammation may be effectively treated by the administration of from about 0.2 to 50 mg of the compound per kilogram of body weight per day (about 20 mg to about 3.5 gms per patient per day). Preferably a dosage of from about 1 mg to about 20 mg per kilogram of body weight per day may produce good results (about 25 mg to about 1 gm per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Bioassay Results Supporting the Utility of the Compounds of the Present Invention It has been found that the compounds of formula (I) exhibit in vitro and in vivo antagonistic activities with respect to PAF:

A. In Vitro Assay: In vitro, they inhibit PAF-induced functions in both the cellular and tissue levels by disturbing the PAF binding to its specific receptor site. The ability of a compound of formula (I) to inhibit the PAF binding to its specific receptor binding site on rabbit platelet plasma membranes was measured by an assay recently developed by us.

The inhibition of $H^3$-PAF binding to the rabbit platelet plasma membrane by a PAF-antagonist of Formula (I) was determined by a method employing isotopic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 μg of the platelet plasma membrane suspension and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabelled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°–5° C.) Tris-buffer solution. Each washed residue was then suspended in 10 ml scintillation solution (Aquasol 2, New England Nuclear, Conn.) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equation:

$$\% \text{ Inhibition} = \frac{(\text{Total binding } C_1) - \text{Total binding with antagonist}}{\text{Specific binding}} \times 100$$

$$\text{Specific binding} = (\text{Total binding } C_1) - (\text{non-specific binding } C_2)$$

From our observation, compounds of formula (I) inhibit in vitro PAF-induced platelet aggregation (rabbit or human platelets); PAF-induced guinea pig peritoneal PMN (polymorphonuclear leukocytes) aggregation; PAF-induced human PMN secretion; and PAF-induced guinea pig smooth muscle concentration. They are also shown in these inhibition studies to be highly specific to PAF. For example, they do not inhibit the binding of $H_1$ antagonist ($^3$H-pyrilamine) to guinea pig brain membrane, nor do they inhibit the binding of a cholecystokinin (CCK) receptor based on an assay on isolated rat pancreas membrane. Furthermore, they affect no or only minute inhibition on the histamine-induced ileum contraction from guinea pigs.

Results from the In Vitro assay

The antagonistic activity of the compounds of structural formula (I) is summarized in the following table:

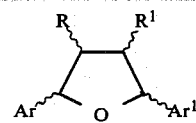

| R | $R^1$ | Ar | $Ar^1$ | isomer | dose (μm) | % inhibition |
|---|---|---|---|---|---|---|
| $CH_3$ | $CH_3$ | 3,4-dimethoxyphenyl | Same as Ar | (2) | 10 | 100 |
| | | | | | 3 | 93 |
| | | | | | 1 | 46 |
| " | " | 3,4-dimethoxyphenyl | Same as Ar | (1) | 5 | 100 |
| | | | | | 1 | 78 |
| | | | | | .3 | 62 |
| | | | | | .1 | 42 |
| $CH_3$ | $CH_3$ | 3,4,5-trimethoxyphenyl | Same as Ar | (1) | 5 | 61 |
| | | | | | 0.5 | 42 |
| " | " | 3,4-dimethoxyphenyl | Same as Ar | (3) | 1 | 68 |
| | | | | | .3 | 37 |
| | | | | | .1 | 32 |
| $CH_3$ | $CH_3$ | 3,4-dimethoxyphenyl | Same as Ar | (5) | 3 | 47 |
| | | | | | .3 | 18 |
| " | " | 3,4-dimethoxyphenyl | Same as Ar | (6) | 3 | 75 |
| | | | | | 1 | 16 |
| $CH_3$ | $CH_3$ | 4-methoxyphenyl | Same as Ar | (1) | 10 | 47 |
| $CH_3$ | $CH_2OCH_3$ | 3,4-dimethoxyphenyl | Same as Ar | (4) | 5 | 62 |
| $CH_3$ | $CH_3$ | phenyl | phenyl | (1) | 5 | 13 |
| $CH_3$ | $CH_3$ | 3-methoxyphenyl | " | (4) | 10 | 49 |
| | | | | | 1 | 28 |
| " | " | 3,4-methylenedioxyphenyl | " | (4) | 10 | 45 |
| | | | | | 1 | 11 |
| $CO_2Et$ | $CO_2Et$ | 3,4-dimethoxyphenyl | Same as Ar | (1) | 1 | 63 |
| $CO_2CH_3$ | $CO_2CH_3$ | 2-chloro-4-hydroxy-5-methoxyphenyl | Same as Ar | (1) | 1 | 15 |
| $CH_3$ | $CH_3$ | 2,5-dimethoxyphenyl | Same as Ar | | 10 | 52 |
| $CO_2CH_3$ | $CH_3$ | 3,4-dimethoxyphenyl | Same as Ar | (4) | 1 | 33 |
| COOH | $CH_3$ | 3,4-dimethoxyphenyl | Same as Ar | (4) | 1 | 18 |
| $CH_3$ | $CH_3$ | 3,4-dimethoxyphenyl | phenyl | (4) | 10 | 100 |
| | | | | | 1 | 9 |
| $CH_3$ | $CH_3$ | 3,4-dimethoxyphenyl | Same as Ar | (4) | 1 | 89 |
| | | | | | .3 | 78 |
| | | | | | .1 | 63 |
| | | | | | .03 | 42 |
| " | " | 3,4,5-trimethoxyphenyl | Same as Ar | (4) | 20 | 68 |
| | | | | | 5 | 48 |
| | | | | | 1 | 12 |
| " | " | 3,4,5-trimethoxyphenyl | Same as Ar | (2) | 20 | 63 |
| | | | | | 5 | 39 |
| | | | | | 1 | 2 |

B. In Vivo Assay

The specific PAF-antagonistic activities are further established by two in vivo assays (Modified procedure of Humphrey et al. Lab. Investigation, 46, 422 (1982)) following the protocols described below:

Method I: Protocol for the evaluation of the oral activity of PAF antagonists or the inhibition of PAF-induced increase of vasopermeability by PAF-antagonists I. Animal species: 5 guinea pigs (400–500 g)
II. Material: 0.5% (w/v) aqueous methylcellulose solution sodium nembutol
   2% Evans Blue solution: 2 g of Evans Blue in 100 ml of pH 7.5 Tris-Buffer solution Tris-Buffer solution: 150 mM NaCl and 10 mM Tris/ml with pH adjusted to 7.5.

Procedure

1. Weigh the guinea pigs. Label them as control, $T_1$, $T_2$, $T_3$ and $T_4$.
2. Fast the animals overnight.
3. Weigh the animals again after the fasting.
4. Ground and suspend a PAF antagonist of formula (I) with intensive sonication in 3 ml of 0.5% aqueous methylcellulose solution.
5. Administer orally to each of the animals $T_1$, $T_2$, $T_3$ and $T_4$ an appropriate amount (in terms of mg/kg of bodyweight) of the antagonist solution from 4., except the control animal which should receive only the 0.5% aq. methylcellulose solution.
6. Forty minutes after the oral administration, anesthetize the animals with sodium nembutol (0.75 ml/kg i.p.).
7. After 30 minutes or when the anesthetics became effective, inject intracardially to each animal 2 ml/kg body weight of the 2% Evans Blue solution.
8. Wait for 10 minutes. In the meantime, shave the backs of the guinea pigs and get ready for the PAF injection. Select two rows of 5 (a total of ten) sites on the back of each animal and designate them as sites
1a, 2a, 3a, 4a, 5a,
1b, 2b, 3b, 4b, 5b,
and inject intracutaneously, in duplicate 0.1 ml of a PAF solution in Tris-buffer or 0.1 ml of the Tris-buffer itself (control) according to the following schedule:

| Sites | Solution to be injected |
|---|---|
| 1a | Tris-buffer |
| 1b | " |
| 2a | $5 \times 10^{-9}$ g/ml PAF |
| 2b | " |
| 3a | $5 \times 10^{-8}$ g/ml PAF |
| 3b | " |
| 4a | $5 \times 10^{-7}$ g/ml PAF |
| 4b | " |
| 5a | $5 \times 10^{-6}$ g/ml PAF |
| 5b | " |

Repeat the same injection on the backs of the remaining animals.

9. Wait for 30 minutes or until the blue color developed into a steady shade on each injection site. Open the chest of each animal, extract by cardiac puncture 1 ml of blood and transfer it to a marked centrifuge tube. Centrifuge all the blood samples at about 2000 xg for 10 minutes and decant the blue tinted supernatants (plasma). Set aside these plasma samples for later spectroscopic measurements.
10. Sacrifice the animals and remove the back skin of each of them. Isolate with a 20 mm diameter steel punch the injection sites (blue spots) into individual discs of skin and dissect each of the skin discs into about 10–20 pieces.
11. Mix in a 50 ml polyethylene test tube the skin pieces from a particular injection site with a medium containing 14 ml of acetone and 6 ml of 0.5% aqueous solution of sodium sulfate. See Harada, M., et al., *J. Pharm. Pharmacol.* 23, 218–219 (1971) for detailed procedures. Repeat the same procedures for each individual injection site.
12. Homogenize the contents of each test tube on a polytron (Kinematica GmbH, Switzerland) with setting at 5 for 10–20 seconds.
13. In the meantime, extract a 100 µl sample of each of the plasma set aside in Step (9) with the same acetone-aqueous sodium sulfate solution used in Step (11). Set aside the resulting extracts for later determination of the Evans blue concentration in the plasma of each animal.
14. Centrifuge the skin preparations from Step (12) for 10 minutes at 750 xg and decant the supernatants for the following spectroscopic determination.
15. Measure the absorbance of each supernatant from Step (14) ("skin sample") as well as the plasma extract from Step (13) ("plasma sample") at 620 nm with a Cary 210 spectrophotometer (Varian, Palo Alto, CA). Calculate the amount of Evans blue in each skin sample in terms of the volume (µl) of the exuded blood plasma according to the following equation:

$$\text{Exuded plasma at a particular injection site (µl)} = \frac{\text{Absorbance (at 620 nm) of "skin sample"}}{\text{Absorbance (at 620 nm) of "plasma sample" of the same animal}} \times 100 \quad \text{(II)}$$

16. Draw a plasma exudation curve. For example, for each of the control and the test animals.
17. Calculate the percent inhibition of PAF-induced cutaneous vascular permeability from measuring the area under the plasma exudation curve of the control animal ($A_C$) and those of the animals treated orally with an antagonist ($A_D$) according to the following equation:

% inhibition observed from the guinea pig treated with x mg/kg of antagonist X.
= $A_C - A_D / A_C \times 100\%$
= $(1 - A_D/A_C) \times 100\%$
= % inhibition at x mg/kg dosage level of antagonist X.

where the ratio $A_D/A_C$ can be determined from the weight of the paper under the plasma exudation curve of the control curve ($A_C$) and that under the plasma exudation curve of the treated animal $T_1$ ($A_D$).

The following table summarizes the in vivo results according to Method I.

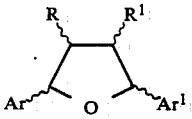

| R | $R^1$ | Ar | $Ar^1$ | isomer | dose (mg/kg PO) | % inhibition |
|---|---|---|---|---|---|---|
| $CH_3$ | $CH_3$ | 3,4-dimethoxyphenyl | Same as Ar | (4) | 50 | 30 |

Method II: Protocol for Assay of Activity of PAF-antagonists administered intravenously (i.v.) in inhibiting PAF-induced symptoms including increased degranulation and decreased arterial blood flow in rats Animals: Female, Wiston rats, 190–220 g
Procedure:

1. Fast rats overnight.
2. Weigh the rats the morning after fasting.
3. Dissolve a test compound in dimethylsulfoxide (DMSO). Dilute test solution 100 fold with PAF solution in Hanks balanced salt solution.
4. Anesthetize the rat with sodium Nembutal (i.p.).
5. Cannulate surgically the left femoral vein and artery of the rat. Take blood sample from artery for basal level values.
6. Infuse through cannulated vein 0.5 ml PAF-test compound solution (0.5 nannomoles PAF per 200 g body weight of the rat). Take blood samples from the cannulated femoral artery at 1.5, 3, 5, 8, 11, 15, 20, 25 and 30 minutes after the infusion.
   (a) the arterial blood flow rate: determined by measuring the time to fill a pre-calibrated 14 $\mu$l capillary tube;
   (b) the vascular permeability: measured by calculating the increased hematocut which results from loss of plasma from the circulation to extra-vascular spaces.
   (c) the circulatory degranulation: determined by assaying the increased plasma level of N-acetyl-glucosaminidase, a marker lysosomal enzyme.
7. Determine the percent change in each parameter of a blood sample at each post-PAF interval including the 30 minute interval, relative to the pre-PAF blood values.
8. Calculate the percent inhibition by the formula:

$$\% \text{ inhibition} = 100 \times \frac{\% \text{ change without test compound} - \% \text{ change with test compound}}{\% \text{ change without test compound}}$$

Results

The inhibition of the PAF-induced responses at an i.v. dose of 50 nonnomoles of all-cis 3,4-dimethyl-2,5-bis-(3,4-dimethoxyphenyl)tetrahydrofuran are 34% for vascular permeability and 38% for degranulation. The all cis isomer of 3,4-dimethyl-2,5-bis-(3,4-dimethoxyphenyl)tetrahydrofuran at an oral dose of 50 mg/kg gave a 49% inhibition of PAF-induced degranulation.

EXAMPLE 1 r-2,t-5-Bis(3,4-dimethoxyphenyl)-c-3,t-4-dimethyl tetrahydrofuran

Step A: Preparation of Racemic-2,3-bis(3,4-dimethoxybenzoyl)butane

To 100 ml of liquid $NH_3$ and 100 mg $FeCl_3$, 1 g of sodium added and stirred for 1 hour at $-40°$ C. To that 7.7 g of 3,4-dimethoxypropiophene was added and stirred for ½ hour, 11 g of $\alpha$-bromo-3,4-dimethoxypropiophenone was added and stirring continued for 1½ hours. At this point, 11 g of ammonium chloride and 200 ml of methylene chloride was added and the temperature allowed to rise to room temperature. Filtration, evaporation and crystallization of the residue from methanol gave 14.5 g of racemic-2,3-bis(3,4-dimethoxybenzoyl)butane as a white solid. ($CDCl_3$): $\delta$1.32 (6H, d, J=7$H_2$), 3.92 and 3.94 (6H each, s, $OCH_3$), 6.8-7.8 (6H, ArH) m.p. 141°-142° C.

Step B: Preparation of r-2,t-5-bis(3,4-dimethoxyphenyl)-c-3,t-4-dimethyltetrahydrofuran The racemic diketone from Step A was reduced with lithium aluminum hydride and 1.0 gram of the resulting diol cyclized as follows: 1.0 g diol, 0.35 g triethylamine in 20 ml of methylenechloride was treated with 0.8 g of methane sulfonyl chloride. After 3 hours of stirring the mixture was treated with 100 ml of ether and the organic layer washed with 1N HCl 5% NaOH and distilled water respectively. Drying ($Na_2SO_4$) and evaporation gave 0.4 g of cis,trans mixture. The major component- -2,t-5-bis-(3,4-dimethoxyphenyl)-c-3,t-4-dimethyl-tetrahydrofuran was recovered by multiple crystallization from hexane. NMR ($CDCl_3$): $\delta$1.05 (6H, d, J 5.4 Hz, $2 \times CH_3$), 1.8 (2H, m, 3-, 4-H), 3.88 and 3.92 (each s, 6H, $2 \times OCH_3$), 4.68 (2H, d, J 8.86 Hz, 2-, 5-H), 6.8–7.1 (6H, m, Ar-H).

EXAMPLE 2 r-2,t-5-Bis(3,4-dimethoxyphenyl)-t-3,c-4-dimethyltetrahydrofuran

One gram of 2,3-bis(3,4-dimethoxyphenyl)-1,4-butanediol prepared in Step B of Example 1 above, 0.4 g 10% Pd/C in 40 ml of acetic acid was stirred over hydrogen at 40 p.s.i. Workup, followed by crystallization from hexane/ether gave 320 mg of r-2,t-5-bis(3,4-dimethoxyphenyl)-t-3,c-4-dimethyltetrahydrofuran. (m.p. 126°-7° C.). NMR ($CDCl_3$): $\delta$1.05 (6H, d, J 6.3 Hz, $2 \times CH_3$), 180 (2H, m, 3-, 4-H), 3.87 and 3.90 (each s, 6H, $2 \times OMe$), 4.67 (2H, d, J 9.3 Hz, 2-,5-H) and 6.90–7.03 (6H, m, ArH).

EXAMPLE 3 r-2,c-5-Bis(3,4-dimethoxyphenyl)-t-3,t-4-dimethyl-tetrahydrofuran

Step A: Preparation of meso-2,3-bis(3,4-dimethoxybenzoyl)butane

One gram of racemic 2,3-bis(3,4-dimethoxybenzoyl)butane in 20 ml THF (warmed to dissolve) was treated with 50 mg of sodium methoxide in 2 ml of methanol followed by 70 ml of ether and stirred overnight. The resulting precipitate was collected by filtration, dissolved in methylene chloride and chromatographed on silica gel column with ethyl acetate-hexane (40:60). 206 mg of the front running band of meso-bis(3,4-dimethoxybenzoyl)butane (206 mg) was obtained. M.p. 188° C.

Step B: Preparation of r-2,c-5-bis(3,4-dimethoxyphenyl)-t-3,t-4-dimethyltetrahydrofuran The meso diketone prepared in Step A (150 mg) was reduced with lithium aluminum hydride and cyclized with methanesulfonyl chloride as shown in Step B of Example 1 to give 38 mg of the major component r-2,c-5-bis(3,4-dimethoxyphenyl)-t-3,t-4-dimethyltetrahydrofuran by crystallization from hexane. NMR ($CDCl_3$): 1.02 (6H, d, J 6.4 Hz, $2 \times CH_3$), 3.90 (12H, s, $4 \times OCH_3$), 4.52 (2H, d, J 6.0, 2-, 5-H).

EXAMPLE 4 r-2, t-5-Bis(3,4-dimethoxyphenyl)-t-3,t-4-dimethyltetrahydrofuran

Hydrogenation of 150 mg of racemic 2,3-bis-(3,4-dimethoxyphenyl)-1,4-butanediol prepared from the meso diketone as shown in Example 3 and subsequent crystallization from hexane gave 24 mg of r-2,t-5-bis(3,4-dimethoxyphenyl)t-3,t-4-dimethyltetrahydrofuran. NMR($CDCl_3$): $\delta$0.64 (3H, d, J=7.0 Hz, $CH_3$), 1.03

(3H, d, J=6.0 Hz, CH₃), 2.36–2.56 (2H, m, 3-H and 4-H), 3.92, (6H, s, 2×OCH₃), 3.93 and 3.94 (3H each, s, OCH₃), 4.69 (1H, d, J=8.8 2-H), 5.49 (1H, d, J=4.0, 5-H), 6.8–7.0 (6H, Ar-H).

EXAMPLE 5 r-2,c-5-Bis(3,4-dimethoxyphenyl)-t-3,c-4-dimethyltetrahydrofuran

Seven grams of racemic diketone from Step A of Example 2 was dissolved in 200 ml of acetic acid, treated with 1.5 g of 10% Pd-C and hydrogenated at 40 psi overnight. Additional 1.5 g of 10% Pd-C was then added and shaking under H₂ continued for 4 hours. Filtration, evaporation and chromatography on silica gel gave 2.8 g of crystalline r-2,c-5-bis(3,4-dimethoxyphenyl)-t-3,c-4-dimethyltetrahydrofuran when eluted with ethyl acetate hexane (40:60). m.p. 121°–122° C.

EXAMPLE 6

All cis-3,4-Dimethyl-2,5-bis(3,4-dimethoxyphenyl)-tetrahydrofuran

One gram of the racemic diketone from Step A of Example 1 dissolved in 4 ml of methylene chloride was refluxed with 5 ml of 5% HCl in methanol for 15 minutes. The mixture was cooled and the crystalline crop of 3,4-dimethyl-2,5-bis(3,4-dimethoxyphenyl)-furan recovered by filtration. M.p. 169°–170° C., yield, 0.75 g. 0.3 Gram of this furan in 20 ml of acetic acid and 3 g of 10% Pd-C stirred over H₂ until 2 equivalents of hydrogen were taken up and workup followed by crystallization from etherchloroform (few drops) gave 0.22 g of the all cis-3,4-dimethyl-2,5-bis(3,4-dimethoxyphenyl)tetrahydrofuran. M.p. 130°–131° C.

What is claimed is:

1. A method for the treatment of a disease or a disorder mediated by PAF comprising administering to a mammalian species in need of the treatment a therapeutically effective amount of a compound of formula:

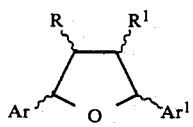

wherein R is:
(a) hydrogen;
(b) lower alkyl of 1–6 carbon atoms;
(c) haloloweralkyl;
(d) halo;
(e) COOH;
(f) CONR²R³ wherein R² and R³ independently represent C₁₋₆ alkyl and hydrogen;
(g) COOR° wherein R° is C₁₋₆alkyl;
(h) loweralkenyl;
(i) —COR²;
(j) —CH₂OR²;
(k) loweralkynyl;
(l) —CH₂NR²R³;
(m) —CH₂SR²;
(n) =O; or
(o) —OR²;

R¹ is lower alkyl; —COOH; or —COOR°; Ar and Ar¹ are the same or different from each other and are
(a) phenyl of formula

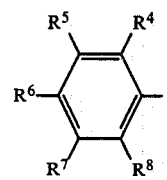

where R⁴–R⁸ independently represent H, RO—, R²S, R²SO, R²SO₂—, CF₃O—, CF₃S—, R²R³N—, —OCH₂CO₂R², —SO₂NR₂R³, —CO₂R², —NR-²SO₂R³, COR², NO₂, or CN or R⁴–R⁵, R⁵–R⁶, R⁶–R⁷ and R⁷–R⁸ are joined together forming a bridge;
(b) pyrryl;
(c) furyl;
(d) pyridyl; or
(e) thiophene.

2. The method of claim 1 wherein the compound is a stereoisomer of formula (4), (1) or (3):

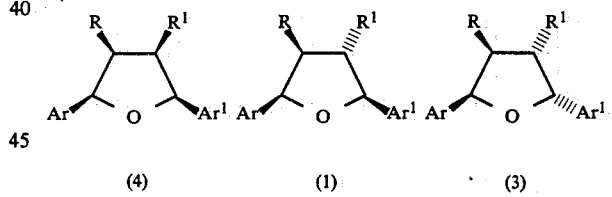

(4)  (1)  (3)

3. The method of claim 1 wherein the active compound is cis-3,4-dimethyl-2,5-bis(3,4-dimethoxyphenyl)-tetrahydrofuran.

* * * * *